US006444852B1

(12) United States Patent
Milburn et al.

(10) Patent No.: US 6,444,852 B1
(45) Date of Patent: Sep. 3, 2002

(54) AMINES USEFUL IN INHIBITING GAS HYDRATE FORMATION

(75) Inventors: Charles R. Milburn, Delawar; Gary M. Sitz, Marysville, both of OH (US)

(73) Assignee: Goldschmidt Chemical Corporation, Hopewell, VA (US)

( * ) Notice: Subject to any disclaimer, the term of this patent is extended or adjusted under 35 U.S.C. 154(b) by 0 days.

(21) Appl. No.: 09/599,094

(22) Filed: Jun. 21, 2000

Related U.S. Application Data

(60) Provisional application No. 60/140,893, filed on Jun. 24, 1999.

(51) Int. Cl.$^7$ .......................... C07C 217/08; C07C 7/20
(52) U.S. Cl. ........................ 564/292; 585/15; 585/899; 585/950
(58) Field of Search ................................ 564/285, 287, 564/292, 294, 293; 585/15, 899, 950

(56) References Cited

U.S. PATENT DOCUMENTS

| 4,915,176 A | 4/1990 | Sugier et al. |
| 5,460,728 A | 10/1995 | Klomp et al. |
| 5,648,575 A | 7/1997 | Klomp et al. |
| 5,879,561 A | 3/1999 | Klomp et al. |

OTHER PUBLICATIONS

Database CAPLUS on STN, Acc. No. 1972:461516, Inai et al., 'Quaternary salts of tris(beta–propoxyethyl) amines.' DE 2155893 abstract.*

* cited by examiner

Primary Examiner—Johann Richter
Assistant Examiner—Brian J. Davis
(74) Attorney, Agent, or Firm—Scully, Scott, Murphy & Presser

(57) ABSTRACT

A novel amine is provided with improved water dispersibility which is useful to modify the formation of hydrates in streams containing low-boiling hydrocarbons and water. The amine-has the formula:

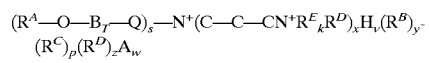

wherein $R^A$ is selected from the group consisting of alkyl, alkenyl, aryl, arylalkyl, arylalkenyl, alkylaryl, and alkenylaryl groups and glycols having from 1 to 24 carbon atoms and optionally contains at least one hetero atom; Q is ethylene, propylene or butylene which may be linear or branched; x is 0 to 4; y and z are each independently 0 to x+1; w is 1 to x+1; v is a number which saturates the nitrogen atom; k and p are independently 0 or 1, with the proviso that k+p is greater than or equal to 1; s is 1, 2 or 3, preferably 1 or 2; T is from 0 to 20; each $R^E$, $R^B$ and $R^C$ is independently selected from the group consisting of straight and branched chain alkyl groups containing 2 to 6 carbon atoms which may optionally be substituted with phenyl, and $R^E$ can be further ($R^A$—O—$B_T$—Q); each $R^D$ is independently selected from the group consisting of hydrogen and straight and branched chain alkyl groups containing 1 to 6 carbon atoms which may optionally be substituted with phenyl; B is a residual of ethylene oxide, propylene oxide or butylene oxide; and A is an anion.

10 Claims, No Drawings

AMINES USEFUL IN INHIBITING GAS HYDRATE FORMATION

RELATED APPLICATIONS

This application claims benefit of U.S. provisional application Serial No. 60/140,893, filed Jun. 24, 1999.

FIELD OF THE INVENTION

The present invention is related to a method of modifying the behavior of gas hydrates to inhibit the plugging of conduits by using a novel amine which includes at least one ether linkage.

BACKGROUND OF THE INVENTION

Gas hydrates are clathrates (inclusion compounds) of gases in a lattice consisting of water molecules. Low-boiling hydrocarbons, such as methane, ethane, propane, butane and iso-butane, are present in natural gas and also in crude oil. Because water may also be present in varying amounts in natural gas and crude oil, the low-boiling gas mixture, under conditions of elevated pressure and reduced temperature, tends to form gas hydrate crystals. The maximum temperature at which gas hydrates can form strongly depends on the pressure of the system. For example, ethane at a pressure of approximately 1 MPa can form hydrates only at temperatures below 4° C., whereas at a pressure of 3 MPa stable hydrates can be present at temperatures as high as 14° C. With respect to this strong dependence of the hydrate melting point on pressure, hydrates differ markedly from ice.

As described by M. von Stackelberg and H. R. Muller (Z. Electrochem. 1954 5825), methane and ethane hydrates form cubic lattices having a lattice constant of 1.2 nm (See, for example, hydrate structure I). The lattice constant of the cubic propane and butane gas hydrates is 1.73 nm (See, for example, hydrate structure II). However, the presence of even small amounts of propane in a mixture of low-boiling hydrocarbons will result in the formation. of gas hydrates having hydrate structure II (J. H. van der Waals and J. C. Platteeuw, Adv. Chem. Phys. 2 1959 1).

It has been known for a long time that gas hydrate crystals, when allowed to form and grow inside a conduit such as a pipeline, tend to block or even damage the conduit. To prevent such blocking, the following thermodynamic measures are possible in principle: removing free water, maintaining elevated temperatures and/or reduced pressures, or adding melting point depressants (antifreeze). In practice, the last-mentioned measure, i.e., the addition of antifreezes, is most often applied. However, the antifreezes, such as the lower alcohols and glycols, have to be added in substantial amounts (several tens of a percent bet weight of the water present) to be effective. An additional disadvantage of such high-amounts is that recovery of the antifreezes is usually required during subsequent processing of the mixtures. Furthermore, at practical dosages, antifreezes may only reduce the kinetics of forming hydrates and, if an extended interruption in flow occurs, damaging hydrates may still form.

An attractive alternative to the anti-hydrate measures described above, particularly the antifreezes, is to use anti-agglomeration inhibitors which modify the hydrate crystal. This crystal modification does not prevent formation of gas hydrates. Instead, anti-agglomeration inhibitors allow small hydrate particles to form which can flow with the oil or gas.

Plants, and animals such as insects and cold-water fish, are known to protect themselves from freezing, both by antifreezes such as glycols and by special peptides and glycopeptides (termed Antifreeze Proteins, AFP's and Antifreeze Glycoproteins, AFGP's) which interfere with ice crystal growth (A. L. de Vries, Comp. Diochem. Physiol, 73 1982 627). Such cold-water fish peptides and glycopeptides have been said to be effective in interfering with the growth of gas-hydrate crystals. However, their production and use for this purpose are considered to be uneconomical.

In PCT Patent Application EP93/01519, the use of polymers and copolymers of N-vinyl-2-pyrrolidone for inhibiting the formation, growth and/or agglomeration of gas hydrate crystals is disclosed.

U.S. Pat. No. 5,460,728 discloses that certain alkylated ammonium, phosphonium and sulphonium compounds are effective in interfering with the growth of gas hydrate crystals and are useful in inhibiting the plugging by gas hydrates of conduits containing low-boiling hydrocarbons and water. The compounds have the formula:

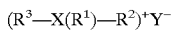

$$(R^3-X(R^1)-R^2)^+Y^-$$

wherein $R^1$, $R^2$ and $R^3$ are independently selected from the group consisting of normal and branched alkyl groups containing at least 4 carbon atoms; X is S, N—$R^4$, or P—$R^4$ where $R^4$ or P—$R^4$ is hydrogen or an organic substituent which may contain one or more hetero atoms such as O and can be in particular alkyl, alkenyl, aryl, arylalkyl, arylalkenyl, alkylaryl, alkenylaryl, or glycol having 1 to 20 carbon atoms; and $Y^-$ is an anion. The preferred ammonium compounds are said to be those compounds in which $R^4$ is alkyl or alkenyl containing 8 to 20 carbon atoms.

U.S. Pat. No. 5,460,728 further discloses that compounds wherein $R^4$ contains more than 12 carbon atoms can provide additional properties, in addition to the inherent hydrate crystal growth-inhibiting properties, such as surface-active properties which help to emulsify the aqueous and hydrocarbon phases (as water-in-oil or oil-in-water emulsions), thereby keeping the concentration of water available for hydrate forming at the conduit wall small. Surface-active properties also help to do the following:

Concentrate the preferred compound near the water-hydrocarbon interfaces, where hydrate formation is most pronounced, thereby raising the local concentration of ions to the freezing-point depressing level.

Modify the structure of water near the hydrocarbon-water interface in such a way that the formation of hydrate crystals is hindered.

Impede further access of water molecules to the hydrate crystal after attachment of the subject compound to the hydrate crystals.

Prevent agglomeration of hydrate crystals by making their surface hydrophobic.

Adhere the subject compound to the conduit wall, thereby preventing the adhesion of hydrates thereto.

The amount of the preferred compounds to be used in the process according to U.S. Pat. No. 5,460,728 is generally between 0.05 and 5 wt. %, preferably between 0.1 and 0.5 wt. %, based on the amount of water in the hydrocarbon-containing mixture.

U.S. Pat. No. 5,879,561 discloses a method for inhibiting the plugging of a conduit containing a flowing mixture of hydrocarbons having from 1 to 8 carbon atoms and water. The method includes the addition of a hydrate formation inhibitor having the formula:

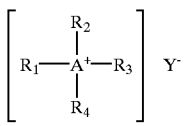

wherein two of $R_1$–$R_4$ are independently normal or branched alkyls having 4 or 5 carbon atoms; two of $R_1$–$R_4$ are independently organic moieties having at least 8 carbon atoms and may contain ester moieties to improve biodegradability; A represents a nitrogen or phosphorus atom; and Y is an anion.

While the prior art compounds may be satisfactory to some extent, there is still a need for compounds which are more hydrophilic, thus providing better water solubility and better dispersibility in antifreeze solutions and which are liquid at lower temperatures thereby providing a higher degree of performance while requiring reduced amounts of the active compound. Furthermore, there is still a need for improved compounds which inhibit the plugging of conduits at lower temperatures, or higher pressures, for longer periods of time than the existing compounds employed in the prior art. It is therefore an object of the present invention to provide improved compounds to inhibit formation of hydrates in streams containing at least some light hydrocarbons and water. It is a further object of the present invention to provide such a method wherein a high concentration of additive is not required.

An even further embodiment of the present invention is to provide improved compounds which do not interfere with the demulsification of the oil when the pressure of the system has been released.

BRIEF SUMMARY OF THE INVENTION

One aspect of the present invention is directed to amine compounds which include ether linkages. Specifically, the amine compounds of the present invention have the following formula:

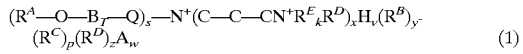
$$(R^A\!-\!O\!-\!B_T\!-\!Q)_s\!-\!N^+(C\!-\!C\!-\!CN^+R^E_kR^D)_xH_v(R^B)_y\!- \quad (1)$$
$$(R^C)_p(R^D)_zA_w$$

wherein $R^A$ is selected from the group consisting of alkyl, alkenyl, aryl, arylalkyl, arylalkenyl, alkylaryl, and alkenylaryl groups and glycols having from 1 to 24, preferably from 3–20, and more preferably from 7 to 18, carbon atoms and optionally contains at least one hetero atom such as oxygen, nitrogen or sulfur;

Q is ethylene, propylene or butylene which may be linear or branched, preferably Q is propylene;

x is 0 to 4;

y and z are each independently 0 to x+1;

w is 1 to x+1;

v is a number which saturates the nitrogen atom;

k and p are independently 0 or 1, with the proviso that k+p is greater than or equal to 1;

s is 1, 2 or 3, preferably 1 or 2;

T is from 0 to 20;

each $R^E$, $R^B$ and $R^C$ is independently selected from the group consisting of straight and branched chain alkyl groups containing 2 to 6 carbon atoms which may optionally be substituted with phenyl, and $R^E$ can be further ($R^A$—O—$B_T$—Q);

each $R^D$ is independently selected. from the group consisting of hydrogen and straight and branched chain alkyl groups containing 1 to 6 carbon atoms which may optionally be substituted with phenyl;

B is a residual of ethylene oxide, propylene oxide or butylene oxide; and

A is an anion.

Another aspect of the present invention is directed to a method for inhibiting the plugging of a conduit, the conduit containing a flowing mixture comprising an amount of hydrocarbons having from one to five carbons and an amount of water wherein the amounts of hydrocarbons and water could form hydrates at conduit temperatures and pressures, the method comprising the steps of:

adding to the mixture an amount of a hydrate formation modifier component of formula (1) in an amount effective to substantially inhibit the formation and/or the agglomeration of hydrates in the mixture at conduit temperatures and pressures; and flowing the mixture containing the hydrate formation modifier through the conduit.

The inventive compounds of formula (1) can also be used to reduce the agglomerization of hydrates and/or to delay the formation of hydrates. In this embodiment of the present invention, an effective amount of at least one compound of formula (1) is added to system which may otherwise form hydrates and their agglomerates.

DETAILED DESCRIPTION OF THE INVENTION

As stated above, the present invention is directed to ether-containing compounds of formula (1) wherein $R^A$ is selected from the group consisting of alkyl, alkenyl, aryl, arylalkyl, arylalkenyl, alkylaryl, and alkenylaryl groups and glycols having from 1 to 24, preferably. from 3–20, and more preferably from 7 to 18, carbon atoms and optionally contains at least one hetero atom such as oxygen, nitrogen or sulfur;

Q is ethylene, propylene or butylene which may be linear or branched, preferably Q is propylene;

x is 0 to 4;

y and z are each independently 0 to x+1;

w is 1 to x+1;

v is a number which saturates the nitrogen atom;

k and p are independently 0 or 1, with the proviso that k+p is greater than or equal to 1;

s is 1, 2 or 3, preferably 1 or 2;

T is from 0 to 20;

each $R^E$, $R^B$ and $R^C$ is independently selected from the group consisting of straight and branched chain alkyl groups containing 2 to 6 carbon atoms which may optionally be substituted with phenyl, and $R^E$ can be further ($R^A$—O—$B_T$—Q);

each $R^D$ is independently selected from the group consisting of hydrogen and straight and branched chain alkyl groups containing 1 to 6 carbon atoms which may optionally be substituted with phenyl;

B is a residual of ethylene oxide, propylene oxide or butylene oxide; and

A is an anion.

More in particular, $R^A$ is preferably linear or branched alkyl having 1 to 24, preferably 3 to 20 and more preferably 7 to 18 carbon atoms. $R^B$, $R^C$ and $R^D$ are preferably independently selected from the group of ethyl, propyl, n-butyl and hydrogen. In some embodiments, each $R_D$ can also be methyl. The anions of the compounds according to the invention can be broadly chosen. Examples include anions such as hydroxide, carboxylate (such as acetate, propionate, butyrate, or benzoate), halide, sulfate, and organic sulfate. Preferred anions are bromide and alkylsulfates. Of the preferred anions, it is most preferably that the anion is bromide, methylsulfate or ethylsulfate.

The most preferred compounds of U.S. Pat. No. 5,460,728 contain either an oleyl or a $C_{12}$ to $C_{18}$ linear fatty moiety which renders the compounds quite hydrophobic. In the present invention, it has surprisingly been discovered that by replacing the fatty moiety with an oxypropylalkyl moiety of a similar range of molecular weight the solubility and the water dispersibility are improved. Surprisingly the resulting compound is not only more dispersible but is in fact, in some instances, soluble in water at room temperature. Even more surprisingly, not only does this improve the ease of application but the effectiveness as a gas hydrate inhibitor is improved significantly.

The compounds of formula (1) according to the present invention can be prepared by procedures which are known in the art using starting materials i.e., reactants which are simple and abundantly available. For instance, the corresponding ether amine can be prepared or acquired and quaternized with a halide such as $R^D$=Br in a solvent such as isopropanol in the presence of a base such as sodium bicarbonate.

When the compounds of formula (1) are used for inhibiting the plugging of a conduit, at least one compound of formula (1) can be added to the mixture of hydrocarbons and water as a liquid or, preferably, in a concentrated solution. The amount of compounds of formula (1) present should comprise 0.05 to 5.0 wt. % based on the weight of water present. Preferably, the amount thereof should be 0.1 to 1.0 wt. % based on the weight of water present. When used in this fashion, these compounds will reduce the speed and/or extent to which gas hydrates agglomerates are formed.

When the compounds of formula (1) are used in reducing the agglomerization of hydrates and/or the delay of hydrate formation, at least one compound of formula (1) is added to the hydrate(s) in an amount such that the compound of formula (1) is present in a concentration of from about 0.05 to about 10, preferably 0.5 to 3, weight % on a solvent-free basis.

The following examples are provided to illustrate the invention and are not intended to be limiting in any way.

EXAMPLE 1

Example 1 demonstrates the preparation of several compounds of formula (1). A typical method used to prepare alkylethertributylammonium bromide is as follows: Charge to a reactor, 1.0 mole of the starting primary amine, 3.0 moles of 1-bromobutane, 2.0 moles of sodium bicarbonate (sodium hydroxide or potassium hydroxide can be substituted for sodium bicarbonate) and sufficient isopropyl alcohol (virtually any low molecular weight alcohol can be substituted for the isopropyl alcohol, i.e., methanol, ethanol, butanol, ethylene glycol, propylene glycol). Seal the reactor and heat to 120°–140° C. Heat at reaction temperature for 5–24 hours to yield a final product with approximately 50–75% quaternary material. Reaction is considered complete when the Total Amine Value (TAV is in mg KOH/gram sample) is less than 1.0. When the reaction is complete, the reactor is cooled and the $CO_2$ gas generated during the reaction is vented. The reaction mixture is then filtered through a filter aid to remove the NaBr formed during the reaction.

Table 1 below contains a listing of samples prepared according to this example, using either 1-bromobutane or alternatively 1-bromopropane.

EXAMPLE 2

This example demonstrates the preparation of several additional compounds of formula (1). Specifically, $C_{12}$–$C_{14}$ ether amine was reductively alkylated using methods commonly known in the art. The resulting tertiary amine was further reacted with various quaternizing agents of acids such as propyl bromide, methyl bromide, hydrogen bromide, dimethyl sulfate, and diethyl sulfate using techniques well known to those skilled in the art and similar to Example 1. Samples made by this method are also listed in Table 1 below.

EXAMPLE 3

This example demonstrates the improved solubility and dispersibility of materials of formula (1) as compared to the preferred compounds of U.S. Pat. No. 5,460,728. The compounds tested are set forth in the following Table 1, CE# denotes a comparative example, whereas S# denotes a compound of the present invention.

TABLE 1

List of Compounds and their Behavior in Water and Brine at 5% Concentration as is

| COMPOUND* | Water | 3.5% Brine |
|---|---|---|
| Oleyl tributyl ammonium bromide (CE1) | Somewhat soluble | Insoluble, dispersion breaks quickly |
| Hexadecyl tributyl ammonium bromide (CE2) | Insoluble | Dispersion breaks slowly |
| $C_{12}$–$C_{14}$ oxypropyl tributylammonium bromide (S1) | Soluble | Insoluble, dispersion breaks slowly |
| $C_{12}$–$C_{14}$ oxypropyl dibutyl methylammonium methyl sulfate (about 10% HBr salt) (S2) | Soluble | Soluble |
| $C_{12}$–$C_{14}$ oxypropyl dibutyl propylammonium bromide (S3) | Soluble | Soluble |
| $C_{12}$–$C_{14}$ oxypropyl dibutyl ethylammonium ethylsulfate (S4) | Soluble | Soluble |
| $C_{12}$–$C_{14}$ oxypropyl dibutyl amino propyl tributylammonium dibromide (S5) | Soluble | Soluble |
| $C_{12}$–$C_{14}$ oxypropyl tripropylammonium bromide (S6) | Soluble | Soluble |
| $C_{12}$–$C_{14}$ oxypropyl dibutyl ammonium hydrobromide (S7) | Soluble | Insoluble, disperses easily |
| iso-$C_7$ oxypropyl tributyl ammonium bromide (S8) | Dispersible | Easily dispersible |
| bis-iso $C_7$ oxypropyl dibutyl ammonium bromide (S9) | Insoluble, dispersion breaks quickly | Insoluble, dispersion breaks quickly |
| $C_{12}$–$C_{14}$ polyethoxy oxypropyl tributyl ammonium bromide (S10) | Soluble | Soluble |

*All compounds contain about 50% HBr salt, unless otherwise specified.

EXAMPLE 4

In order to determine the effectiveness of various materials in modifying gas hydrate behavior a 300 ml Autoclave Engineers stirred reactor was fitted with an "anchor" style agitator and the reactor itself was mounted thru a low friction bearing so that the torque transmitted from the agitator to the reactor could be measured and recorded. The agitator was driven at 40 rpm with a loose v-belt which allowed the agitator to seize at reasonably low torque.

The reactor was submerged in a glycol bath in a jacketed beaker which was cooled with a circulating glycol bath whose temperature was determined by a programmable controller. This program was to hold at 60° F. for 30 minutes and then cool to about 20° F. at a rate of 2° F./hour, holding at that temperature for as long as needed. For each experiment, the reactor was charged with 120 grams of salt water brine, containing 3.5% NaCl.

The various compounds were added to the brine at the levels noted below. The reactor was then pressurized to about 1100 to 1200 psi with a gas mixture containing 85% methane, 10% ethane and 5% propane.

The indication of crystallization is either an increase in torque or a rise in autoclave temperature due to the heat of crystallization. The results are shown in Table 2 below.

TABLE 2

| Additive Sample | Amount Used (Solvent free) (gms) | Pressure (PSIG) | Autoclave Temp. at first sign of crystallization, either exothermic or torque increase (° F.) | Duration of Crystallization until Agitator Seized (hrs) | Total hrs. from time temp. decreases from 60° F. |
|---|---|---|---|---|---|
| CE1 | 1.21 | 1100–1000 | 51 | 5 | 13 |
| S1 | 1.21 | 1000 | 55 | 12 | 15.5 |
| S1 | 1.21 | 1100 | 30 | 2.5 | 20.5 |
| S1 | 1.21 | 1150 | 32 | 1.5 | 19.0 |
| S2 | 1.17 | 900–1180* | 33 | 3 | 18.5 |
| S3 | 1.17 | 1100 | 35 | 2.5 | 18 |
| S4 | 1.24 | 1100 | 36 | 2.5 | 18.5 |
| S5 | 1.83 | 1100 | 28 | 3.5 | 24 |
| S6 | 1.12 | 1070 | 29 | 4.5 | 38.5 |
| S7 | 1.11 | 1180 | 36 | .75 | 21 |
| S8 | 1.04 | 1050 | 26 | 5 | 26 |
| S9 | 1.23 | 1180 | 29 | 5.5 | 24 |
| S10 | 1.83 | 1180 | 35 | 10 | 28 |

*Pressure dropped during crystallization from 1180 to 900.

It is noted that lower temperatures for the onset of crystallization are beneficial as is also a longer time during which crystallization occurs before the agitator seizes. As the degree of subcooling increases, it is not surprising that in some cases the time of crystallization decreases. Since all the experiments were carried out with the same coolant temperature program, the total time from the start of the coolant temperature decline from 60° F. to agitator seizure is also a measure of performance. Thus, it is clear that the ether amines of the present invention tested are superior to those of the prior art.

EXAMPLE 5

This example demonstrates that the inventive compounds are effective in substantially preventing the agglomerization of gas hydrates in the presence of crude oil. In the tests performed herein, samples of Gulf of Mexico crude oil were combined in water containing 3.5% NaCl and 1.125% of the inventive compound sample, S1 (See, Table 1), (on a solvent-free basis); the oil to water ratios of 70:30 and 50:50 were used.

A comparative test was carried out with 2.5% of a prior art gas hydrate inhibitor which functions by emulsifying the sample. The comparative test was carried out at a 50:50 oil to water ratio.

Synthetic natural gas used in this example had the following composition: 81.3% methane, 9.3% ethane, 5.4% propane, 0.9% iso-butane, 1.7% N-butane, 0.4% iso-pentane, 0.2% N-pentane. and 0.3% carbon dioxide, 0.4% nitrogen.

The crude oil was heated to 150° F. to dissolve waxes. The oil and water phases were charged (120 ml total) to a 300 ml high-pressure autoclave at 86° F. and pressured to 3300 psi with good agitation (500 rpm). To saturate the liquid with gas, after 30 minutes, the agitation was reduced to 100 rpm and the autoclave was cooled at 10° F./hr to 40° F., at which time, agitation was stopped and the 40° F. temperature was maintained for 16 hours.

After the 16 hour time period, agitation was restarted at 500 rpm to determine the torque required and the experiment was run for 5 hours, if possible. The autoclave was then rapidly depressurized and the state of the hydrates was observed.

For Sample S1 used at 1.125% on a solvent-free basis in salt water at both 70:30 and 50:50 ratios, the resulting hydrates were very small particles which were creamy in texture. No gas hydrates were observed on the walls of the reactor. However, for a comparative standard product X used at 2.5%, large hydrate particles, some greater than ½ inch were found having the consistency of snow.

The above experiments clearly demonstrate that S1 is highly effective as an anti-agglomeration agent at low use levels.

EXAMPLE 6

This example demonstrates the ability of the inventive compounds to be used on the subsequent demulsification of synthetic seawater from crude oil. Specifically, the following experiment was carried out using both Alaskan crude oil and Gulf of Mexico crude oil:

The specific-type of crude oil containing seawater (e.g., brine) was heated to 80° C. to dissolve any waxes that may be presented therein. A mixture of crude and seawater containing 0.75% (solvent-free basis) of agent S1, based on the weight % of brine in the seawater, was then made having a ratio of oil to brine of 70:30. The mixture was allowed to equilibrate to 25° C. and was then mixed at 800 rpm for 30 seconds to achieve uniformity.

After achieving uniformity, the mixture was mixed at 8000 rpm for 30 seconds to form an emulsion. The emulsion was poured into a 50 ml BS+N tubes and the amount of seawater was noted at intervals of 0, 2, 5, 10, 15, 20, 30, 45 and 60 minutes. The experiment was carried out in triplicate and the average of the three runs are reported hereinbelow in Table 3.

TABLE 3

RATE OF DEMULSIFICATION AS INDICATED BY ml of SEPARATED WATER

| Time (min) | ALASKAN CRUDE | | GULF OF MEXICO | |
|---|---|---|---|---|
| | Blank | 0.75% S1 | Blank | 0.75% S1 |
| 0 | 0 | 0 | 0 | 0 |
| 2 | 0 | 0.5 | 0.25 | 0.25 |
| 5 | 0 | 4.00 | 0.45 | 4.67 |
| 10 | 0 | 11.50 | 1.0 | 14.83 |
| 15 | 0.25 | 12.67 | 1.5 | 15.00 |
| 20 | 0.25 | 13.17 | 1.72 | 15.17 |
| 30 | 0.25 | 13.33 | 2.17 | 15.17 |
| 45 | 0.25 | 13.33 | 2.68 | 15.33 |
| 60 | 0.25 | 13.33 | 3.08 | 15.37 |

While the present invention has been particularly shown and described with respect to preferred embodiments thereof, it will be understood by those skilled in the art that the foregoing and other changes in form and detail may be made without departing from the spirit and scope of the present invention. It is therefore intended that the present

What is claimed is:

1. A compound of formula (1)

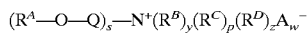 (1)

wherein $R^A$ is a $C_{12-14}$ alkyl;

Q is propylene which may be linear or branched;

s is 1;

s+y+p+z=4;

w is 1;

each $R^B$, $R^C$ and $R^D$ is independently butyl or pentyl which may be a straight chain or branched; and A is an anion.

2. The compound of claim 1 wherein $R^B$, $R^C$, and $R^D$ are each independently selected from the group consisting of butyl and isobutyl.

3. The compound of claim 1 wherein A is selected from the group consisting of hydroxide, carboxylate, halide, sulfate, and organic sulfate.

4. The compound of claim 1 wherein A is bromide, methylsulfate or ethylsulfate.

5. A method for reducing the agglomerization of hydrates of hydrocarbons containing 1 to 5 carbon atoms, or decaying the formation of said hydrates comprising adding thereto an effective amount of at least one compound having the formula:

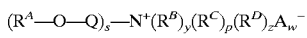 (1)

wherein $R^A$ is a $C_{12-14}$ alkyl;

Q is propylene which may be linear or branched;

s is 1;

s+y+p+z=4;

w is 1;

each $R^B$, $R^C$ and $R^D$ is independently butyl or pentyl which may be a straight chain or branched; and A is an anion.

6. The method of claim 5 wherein said compound is present in a concentration of 0.05 to 10.0 weight %, based on the amount of water available to form hydrate.

7. The method of claim 6 wherein said compound is present in a concentration of 0.5 to 3 weight % based on the amount of water available to form hydrate.

8. The method of claim 5 wherein $R^B$, $R^C$, and $R^D$ are each independently selected from the group consisting of butyl and isobutyl.

9. The method of claim 5 wherein A is selected from the group consisting of hydroxide, carboxylate, halide, sulfate, and organic sulfate.

10. The method of claim 5 wherein A is bromide, methylsulfate or ethylsulfate.

* * * * *